US012747196B2

(12) United States Patent
Hicks et al.

(10) Patent No.: US 12,747,196 B2
(45) Date of Patent: Sep. 29, 2026

(54) SYSTEMS AND METHODS FOR PROCESSING GAS STREAMS

(71) Applicant: University of Notre Dame du Lac, South Bend, IN (US)

(72) Inventors: Jason Christopher Hicks, South Bend, IN (US); Gerardo Rivera-Castro, South Bend, IN (US)

(73) Assignee: University of Notre Dame du Lac, South Bend, IN (US)

( * ) Notice: Subject to any disclaimer, the term of this patent is extended or adjusted under 35 U.S.C. 154(b) by 522 days.

(21) Appl. No.: 18/345,908

(22) Filed: Jun. 30, 2023

(65) Prior Publication Data

US 2024/0010582 A1 Jan. 11, 2024

Related U.S. Application Data

(60) Provisional application No. 63/367,649, filed on Jul. 5, 2022.

(51) Int. Cl.

*C07C 2/80* (2006.01)
*B01J 8/02* (2006.01)
*B01J 29/48* (2006.01)

(52) U.S. Cl.

CPC ............... *C07C 2/80* (2013.01); *B01J 8/0278* (2013.01); *B01J 8/0285* (2013.01); *B01J 29/48* (2013.01);

(Continued)

(58) Field of Classification Search

CPC . C07C 2/80; C07C 2529/076; C07C 2529/40; C07C 2529/48; B01J 8/0278; B01J 8/0285; B01J 29/48; B01J 2208/00805; B01J 2208/00973; B01J 19/088; B01J 2219/0809; B01J 2219/0833; B01J 2219/0835; B01J 2219/0875; B01J 2219/0886; B01J 29/40; B01J 29/46

See application file for complete search history.

(56) References Cited

U.S. PATENT DOCUMENTS

2022/0362731 A1* 11/2022 Skoptsov ............... B01J 19/126
2023/0183588 A1* 6/2023 Al-Qahtani ............. C10L 3/104 423/302
2024/0286107 A1* 8/2024 Zhou ........................ B01J 8/065

FOREIGN PATENT DOCUMENTS

CN 111234864 A 6/2020
CN 112114026 A 9/2020

(Continued)

OTHER PUBLICATIONS

Li et al. ("A process for a high yield of aromatics from the oxygen-free conversion of methane: combining plasma with Ni/HZSM-5 catalysts", Green Chem., 2007, 9, 647-653). (Year: 2007).*

(Continued)

*Primary Examiner* — Ali Z Fadhel

(74) *Attorney, Agent, or Firm* — Michael Best & Friedrich LLP

(57) ABSTRACT

Exemplary systems and methods process gas streams comprising methane. Exemplary reactors receive a gas stream and comprise catalyst material in a reaction zone. Nonthermal plasma may be generated in the reaction zone. A temperature of the reaction zone may be maintained within a predetermined temperature range. Products may be collected from a reactor outlet.

19 Claims, 4 Drawing Sheets

(52) U.S. Cl.
CPC ................ *B01J 2208/00805* (2013.01); *B01J 2208/00973* (2013.01); *C07C 2529/076* (2013.01)

(56) References Cited

FOREIGN PATENT DOCUMENTS

| | | | | |
|---|---|---|---|---|
| WO | 2015035518 A1 | | 3/2015 | |
| WO | WO-2021164136 A1 | * | 8/2021 | ............ C10G 50/00 |

OTHER PUBLICATIONS

Translation of WO 2021164136 A1 (Year: 2021).*
Bai, M. et al. Conversion of Methane to Liquid Products, Hydrogen, and Ammonia with Environmentally Friendly Condition-Based Microgap Discharge. J Air Waste Manage Assoc 2008, 58 (12), 1616-1621.
Barboun, P. et al. Distinguishing Plasma Contributions to Catalyst Performance in Plasma-Assisted Ammonia Synthesis. ACS Sustain Chem Eng 2019, 7 (9), 8621-8630.
Bogaerts, A. et al. The 2020 Plasma Catalysis Roadmap. J. Phys. D: Appl. Phys. 2022, 53, 443001.
Conrad, M. A. et al. Insights into the Chemistry of the Homogeneous Thermal Oligomerization of Ethylene to Liquid- Fuel-Range Hydrocarbons. Ind Eng Chem Res 2023, 62 (5), 2202-2216.
Diefenbach, M. et al. HCN Synthesis from Methane and Ammonia: Mechanisms of Pt+-Mediated C—N Coupling. J Am Chem Soc 1999, 121 (45), 10614-10625.
Gautier, T., et al. "Nitrile gas chemistry in Titan's atmosphere." Icarus 213.2 (2011): 625-635.
Hawtof, R. et al. Catalyst-Free, Highly Selective Synthesis of Ammonia from Nitrogen and Water by a Plasma Electrolytic System. Sci. Adv. 2019, 31 (2).
Heintze, M., et al. "Methane conversion into aromatics in a direct plasma-catalytic process." Journal of Catalysis 206.1 (2002): 91-97.
Horvath, G. et al. Organic Chemistry of NH3 and HCN Induced by an Atmospheric Abnormal Glow Discharge in N2—CH4 Mixtures. EPJ Applied Physics 2011, 53 (1) 11001.
Horvath, G. et al. Packed Bed DBD Discharge Experiments in Admixtures of N 2and CH 4. Plasma Chemistry and Plasma Processing 2010, 30 (5), 565-577.
Imanaka, H. et al. Formation of Nitrogenated Organic aerosols in the Titan Upper Atmosphere. PNAS 2010, 107, 12423-12428.
Imanaka, H. et al. Laboratory Experiments of Titan Tholin Formed in Cold Plasma at Various Pressures: Implications for Nitrogen-Containing Polycyclic Aromatic Compounds in Titan Haze. Icarus 2004, 168 (2), 344-366.
Kim, J. et al. Enhancing C—H Bond Activation of Methane via Temperature-Controlled, Catalyst-Plasma Interactions. ACS Energy Lett 2016, 1 (1), 94-99.
Kogelschatz, U. Dielectric-Barrier Discharges: Their History, Discharge Physics, and Industrial Applications. Plasma Chemistry and Plasma Processing 2003, 23, 1-46.
Li, X.-S. et al. "A Process for a High Yield of Aromatics from the Oxygen-Free Conversion of Methane: Combining Plasma with Ni/HZSM-5 Catalysts," Green Chem. (2007) 9: pp. 647-653.
Li, X.-S. et al. "High Yield of Aromatics from CH4 in a Plasma-Followed-by-Catalyst (PFC) Reactor," AIChE J. (2006) 52: pp. 3321-3324.
Li, X.-S. et al. "Pulsed Streamer Discharge Plasma over Ni/HZSM-5 Catalysts for Methane Conversion to Aromatics at Atmospheric Pressure," Plasma Process. Polym. (2007) 4: pp. 15-18.
Mehta, P. et al. Catalysis Enabled by Plasma Activation of Strong Chemical Bonds: A Review. ACS Energy Letters 2019, 1115-1133.
Morrison, M. et al. Titan's Organic Aerosols_ Molecular Composition and Structure of Laboratory Analogues Inferred from Pyrolysis Gas Chromatography Mass Spectrometry Analysis. Icarus 2016, 227, 442-454.
Park, S., et al. "Plasma-assisted non-oxidative conversion of methane over Mo/HZSM-5 catalyst in DBD reactor." Topics in Catalysis 60 (2017): 735-742.
Ramírez, S. I. et al. Organic Chemistry Induced by Corona Discharges in Titan's Troposphere: Laboratory Simulations. Advances in Space Research, 2005, 36, 274-280.
Ruiz-Castillo, P. et al. Applications of Palladium-Catalyzed C—N Cross-Coupling Reactions. Chemical Reviews. American Chemical Society 2016, 12564-12649.
Scarduelli, G., et al. "Methane oligomerization in a dielectric barrier discharge at atmospheric pressure." Plasma Processes and Polymers 6.1 (2009): 27-33.
Sholl, D. S. et al. Seven Chemical Separtions to Change the World. Nature 2016, 532, 435-437.
Snoeckx, R. et al. Influence of N2 Concentration in a CH4/N2 Dielectric Barrier Discharge Used for CH4 Conversion into H 2. Int J Hydrogen Energy 2013, 38 (36), 16098-16120.
Somogyi, A. et al. Organic Environments on Saturn's Moon, Titan: Simulating Chemical Reactions and Analyzing Products by FT-ICR and Ion-Trap Mass Spectrometry. J Am Soc Mass Spectrom 2005, 16 (6), 850-859.
Szopa, C. et al. PAMPRE_ A Dusty Plasma Experiment for Titan's Tholins Production and Study. Planet. Space Sci. 2006, 54, 394-404.
Thompson, W. R., et al. "Plasma discharge in N2+ CH4 at low pressures: experimental results and applications to Titan." Icarus 90.1 (1991): 57-73.
Torborg, C.; et al. Recent Applications of Palladium-Catalyzed Coupling Reactions in the Pharmaceutical, Agrochemical, and Fine Chemical Industries. Advanced Synthesis and Catalysis. 2009, 3027-3043.
Torokova, L. et al. Atmospheric Pressure Glow Discharge Generated in Nitrogen-Methane Gas Mixture: PTR-MS Analyzes of the Exhaust Gas. In EPJ Applied Physics 2015, 71 (2), 20806.
Torokova, L., et al. "Gas Chromatography Analysis of Discharge Products in N2—CH4 Gas Mixture at Atmospheric Pressure: Study of Mimic Titan's Atmosphere." Contributions to Plasma Physics 55.6 (2015): 470-480.
Truica-Marasescu, F. et al. "Nitrogen-rich plasma polymers: Comparison of films deposited in atmospheric- and low-pressure plasmas." Thin solid films 516.21 (2008): 7406-7417.
Truica-Marasescu, F. et al. Nitrogen-Rich Plasma-Polymer Films for Biomedical Applications. Plasma Processes and Polymers 2008, 5 (1), 44-57.
Vuitton, V. et al. Ion chemistry and N-containing molecules in Titan's upper atmosphere. Icarus. 2007, 191 (15) 722-742.
Wang, L. et al. One-Step Reforming of CO 2 and CH 4 into High-Value Liquid Chemicals and Fuels at Room Temperature by Plasma-Driven Catalysis. Angewandte Chemie 2017, 129 (44), 13867-13871.
Yasuda, H., et al. "Plasma polymerization of some organic compounds and properties of the polymers." Journal of Polymer Science: Polymer Chemistry Edition 14.1 (1976): 195-224.

* cited by examiner

SYSTEMS AND METHODS FOR PROCESSING GAS STREAMS

CROSS-REFERENCE TO RELATED APPLICATION(S)

This application claims priority to U.S. Provisional Patent Application No. 63/367,649 filed on Jul. 5, 2022, the entire contents of which are incorporated herein by reference.

STATEMENT OF GOVERNMENT INTEREST

This invention was made with government support under DE-FE0031862 awarded by the U.S. Department of Energy (DOE). The government has certain rights in the invention.

TECHNICAL FIELD

The present disclosure relates to materials, methods, and techniques for processing gas streams. Exemplary gas streams may comprise methane. Exemplary systems and methods for processing gas streams may generate various aromatic compounds.

INTRODUCTION

Methane ($CH_4$), the most abundant hydrocarbon available in natural gas resources, is a valuable fossil energy source and an important chemical feedstock. However, without direct pipeline access, the transportation of $CH_4$ from remote locations is challenging and leads to feedstock misutilization through gas flaring and/or venting. Improved methods for the on-site conversion of $CH_4$ to condensable and transportable liquids, such as olefins and aromatics are needed.

SUMMARY

The present disclosure relates to systems and methods for processing gas streams.

In one aspect, a method for processing a gas stream is disclosed. An exemplary method may include providing the gas stream to a reactor, the gas stream comprising methane and being provided at a first flowrate; contacting the gas stream with a catalyst material in a reaction zone of the reactor; providing a voltage to an inner electrode disposed within the reaction zone, thereby generating a plasma in the reaction zone across a discharge gap; maintaining a temperature in the reaction zone of no less than 300° C. and no greater than 700° C.; collecting products from an outlet of the reactor.

In another aspect, a system for processing a gas stream comprising methane is disclosed. An exemplary system may comprise a reactor, an analysis unit, and a voltage supply and monitor system. The reactor may comprise a first inlet in fluid communication with a gas stream source, the gas source comprising methane; a reaction zone in fluid communication with the first inlet, the reaction zone comprising a catalyst bed, an inner electrode, an outer electrode, and an inner volume defined between the inner electrode and the outer electrode; the reactor may also comprise a reactor temperature regulation unit arranged to maintain a predetermined reaction zone temperature of no less than 300° C. and no greater than 700° C.; and an outlet in fluid communication with the reaction zone. The analysis unit may be configured to receive fluid from the reactor outlet. The voltage supply and monitor system may be in electrical communication with the inner electrode and with the outer electrode.

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways.

DETAILED DESCRIPTION

Figure 1:
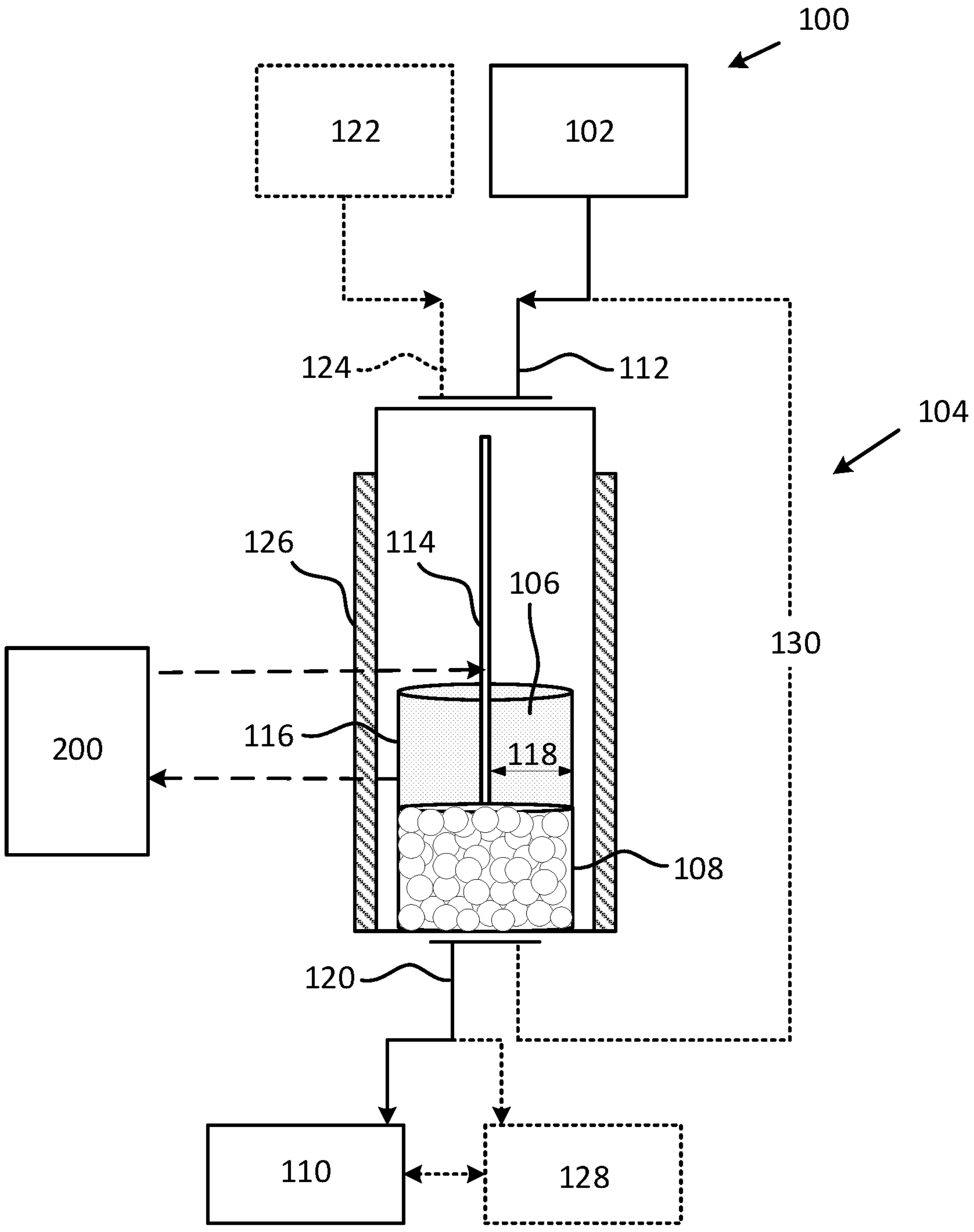
FIG. 1 is a schematic depiction of an exemplary system for processing a gas stream.

Exemplary materials, methods and techniques disclosed and contemplated herein generally relate to gas stream processing systems and methods. Exemplary gas stream processing systems may be configured to process a gas stream, such as a gas stream comprising methane, and generate fluid products. Exemplary gas stream processing methods described herein may generate various aromatic compounds.

I. DEFINITIONS

Unless otherwise defined, all technical and scientific terms used herein have the same meaning as commonly understood by one of ordinary skill in the art. In case of conflict, the present document, including definitions, will control. Methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "about" is used to indicate that exact values are not necessarily attainable. Therefore, the term "about" is used to indicate this uncertainty limit. The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5-1.4. The modifier "about" should also be considered as disclosing the range defined by the absolute values of the two endpoints. For example, the expression "from about 2 to about 4" also discloses the range "from 2 to 4."

For the recitation of numeric ranges herein, each intervening number there between with the same degree of precision is contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are contemplated. For another example, when a pressure range is described as being between ambient pressure and another pressure, a pressure that is ambient pressure is expressly contemplated.

The term "alkene" as used herein, means a straight or branched, hydrocarbon containing at least one carbon-carbon double bond. The term "$C_{2-4}$ alkene" means a straight or branched chain hydrocarbon containing from 2 to 4 carbon atoms and at least one carbon-carbon double bond.

The term "alkyne" as used herein, means a straight or branched, hydrocarbon containing at least one carbon-carbon triple bond.

The term "non-thermal plasma" as used herein, means a plasma which is not in thermodynamic equilibrium with the immediate environment. "Non-thermal plasma" is alternatively referred to in literature as "cold plasma" or "non-equilibrium plasma."

II. EXEMPLARY MATERIALS

Exemplary methods and techniques process and generate various materials. Exemplary gas stream processing materials include gas streams, catalyst materials, and products, various aspects each of which are discussed below.

A. Exemplary Gas Compositions

1. Exemplary Gas Streams

Exemplary gas streams may include various gases. Exemplary gas streams may comprise methane ($CH_4$). In various instances, exemplary gas streams may comprise methane ($CH_4$) and one or more additional components, such as, ethane ($C_2H_6$), propane ($C_3H_8$), butane ($C_4H_{10}$), and combinations thereof. In various instances, exemplary gas streams may comprise various amounts of various constituents.

Exemplary gas streams may comprise methane ($CH_4$) at 1 mole % (mol %) to 100 mol %. In various instances, exemplary gas streams may comprise methane ($CH_4$) at 1 mol % to 99 mol %; mol % to 95 mol %; 10 mol % to 90 mol %; 15 mol % to 85 mol %; 20 mol % to 80 mol %; 25 mol % to 75 mol %; 30 mol % to 70 mol %; 35 mol % to 65 mol %; 40 mol % to 60 mol %; or 45 mol % to mol %. In various instances, exemplary gas streams may comprise methane ($CH_4$) at no greater than 100 mol %; no greater than 90 mol %; no greater than 80 mol %; no greater than 75 mol %; no greater than 70 mol %; no greater than 60 mol %; no greater than 50 mol %; no greater than 40 mol %; no greater than 30 mol %; no greater than 25 mol %; no greater than 20 mol %; no greater than 15 mol %; no greater than 10 mol %; or no greater than 5 mol %. In various instances, exemplary gas streams may comprise methane ($CH_4$) at no less than 1 mol %; no less than 5 mol %; no less than 10 mol %; no less than 15 mol %; no less than 20 mol %; no less than 25 mol %; no less than 30 mol %; no less than 40 mol %; no less than 50 mol %; no less than 60 mol %; no less than mol %; no less than 75 mol %; no less than 80 mol %; no less than 90 mol %; or no less than 95 mol %.

Exemplary gas streams may comprise ethane ($C_2H_6$), when present, at 2 mol % to 20 mol %. In various instances, exemplary gas streams may comprise ethane ($C_2H_6$) at 2 mol % to 19 mol %; 2 mol % to 10 mol %; 10 mol % to 20 mol %; 4 mol % to 18 mol %; or 8 mol % to 14 mol %. In various instances, exemplary gas streams may comprise ethane ($C_2H_6$), when present, at no greater than 20 mol %; no greater than 18 mol %; no greater than 16 mol %; no greater than 14 mol %; no greater than 12 mol %; no greater than 10 mol %; no greater than 8 mol %; no greater than 6 mol %; no greater than 4 mol %; or no greater than 3 mol %. In various instances, exemplary gas streams may comprise ethane ($C_2H_6$), when present, at no less than 2 mol %; no less than 3 mol %; no less than 5 mol %; no less than 7 mol %; no less than 9 mol %; no less than 11 mol %; no less than 13 mol %; no less than 15 mol %; no less than 17 mol %; or no less than 19 mol %.

Exemplary gas streams may comprise propane ($C_3H_8$), when present, at 0.5 mol % to 10 mol %. In various instances, exemplary gas streams may comprise propane ($C_3H_8$) at 0.5 mol % to mol %; 0.5 mol % to 5 mol %; 5 mol % to 10 mol %; 2 mol % to 8 mol %; or 4 mol % to 6 mol %. In various instances, exemplary gas streams may comprise propane ($C_3H_8$), when present, at no greater than 10 mol %; no greater than 9 mol %; no greater than 8 mol %; no greater than 7 mol %; no greater than 6 mol %; no greater than 5 mol %; no greater than 4 mol %; no greater than 3 mol %; no greater than 2 mol %; or no greater than 1 mol %. In various instances, exemplary gas streams may comprise propane ($C_3H_8$), when present, at no less than 0.5%; no less than 1 mol %; no less than 2 mol %; no less than 3 mol %; no less than 4 mol %; no less than 5 mol %; no less than 6 mol %; no less than 7 mol %; no less than 8 mol %; or no less than 9 mol %.

Exemplary gas streams may comprise butane ($C_4H_{10}$), when present, at 0.2 mol % to 5 mol %. In various instances, exemplary gas streams may comprise butane ($C_4H_{10}$) at 0.2 mol % to mol %; 0.5 mol % to 2.5 mol %; 2.5 mol % to 5 mol %; 1 mol % to 3 mol %; or 3 mol % to 5 mol %. In various instances, exemplary gas streams may comprise butane ($C_4H_{10}$), when present, at no greater than 5 mol %; no greater than 4 mol %; no greater than 3 mol %; no greater than 2 mol %; no greater than 1 mol %; or no greater than 0.5 mol %. In various instances, exemplary gas streams may comprise butane ($C_4H_{10}$), when present, at no less than 5 mol %; no less than 4 mol %; no less than 3 mol %; no less than 2 mol %; no less than 1 mol %; or no less than 0.5 mol %.

2. Exemplary Additional Gases

In various instances, various additional gases may be added to exemplary gas streams. In some instances, additional gases may be inert. The term "inert gas," as used herein, means a gas that will not react or be modified during gas stream processing.

Exemplary additional gases include nitrogen ($N_2$) gas, helium (He), neon (Ne), argon (Ar), krypton (Kr), xenon (Xe), radon (Rn), and combinations thereof. In some instances, the additional gas may comprise nitrogen ($N_2$), helium (He) and/or argon (Ar).

In some instances, nitrogen ($N_2$) gas may be added to an exemplary gas stream comprising methane ($CH_4$), thereby forming a gas composition comprising methane ($CH_4$) and additional nitrogen ($N_2$).

Exemplary gas compositions comprising methane ($CH_4$) and additional nitrogen ($N_2$) gas may comprise methane ($CH_4$) at 1 mol % to 99 mol %. In various instances, exemplary gas compositions may comprise methane ($CH_4$) at 5 mol % to 95 mol %; 10 mol % to 90 mol %; 15 mol % to 85 mol %; 20 mol % to 80 mol %; 25 mol % to 75 mol %; 30 mol % to 70 mol %; 35 mol % to 65 mol %; 40 mol % to 60 mol %; or 45 mol % to 65 mol %. In various instances, exemplary gas compositions comprising methane ($CH_4$) and additional nitrogen ($N_2$) gas may comprise methane ($CH_4$) at no greater than 99 mol %; no greater than 90 mol %; no greater than 80 mol %; no greater than 75 mol %; no greater than 70 mol %; no greater than 60 mol %; no greater than 50 mol %; no greater than 40 mol %; no greater than 30 mol %; no greater than 25 mol %; no greater than 20 mol %; no greater than 15 mol %; no greater than 10 mol %; or no greater than 5 mol %. In various instances, gas compositions comprising methane ($CH_4$) and additional nitrogen ($N_2$) gas may comprise methane ($CH_4$) at no less than 1 mol %; no less than 5 mol %; no less than 10 mol %; no less than 15 mol %; no less than 20 mol %; no less than 25 mol %; no less than 30 mol %; no less than 40 mol %; no less than 50 mol %; no less than 60 mol %; no less than 70 mol %; no less than 75 mol %; no less than 80 mol %; no less than 90 mol %; or no less than 95 mol %.

Exemplary gas compositions comprising methane ($CH_4$) and additional nitrogen ($N_2$) gas may comprise nitrogen ($N_2$) at 1 mol % to 99 mol %. In various instances, exemplary gas compositions comprising methane ($CH_4$) and additional nitrogen ($N_2$) gas may comprise nitrogen ($N_2$) at 5 mol % to 95 mol %; 10 mol % to 90 mol %; 15 mol % to 85 mol %; 20 mol % to 80 mol %; 25 mol % to 75 mol %; 30 mol % to 70 mol %; 35 mol % to 65 mol %; 40 mol % to 60 mol %; or 45 mol % to 65 mol %. In various instances, exemplary gas compositions comprising methane ($CH_4$) and additional nitrogen ($N_2$) gas may comprise nitrogen ($N_2$) at no greater than 99 mol %; no greater than 90 mol %; no greater than 80 mol %; no greater than 75 mol %; no greater than 70 mol %; no greater than 60 mol %; no greater than 50 mol %; no greater than 40 mol %; no greater than 30 mol %; no greater than 25 mol %; no greater than 20 mol %; no greater than 15 mol %; no greater than 10 mol %; or no greater than 5 mol %. In various instances, exemplary gas compositions comprising methane ($CH_4$) and additional nitrogen ($N_2$) gas may comprise nitrogen ($N_2$) at no less than 1 mol %; no less than 5 mol %; no less than 10 mol %; no less than 15 mol %; no less than 20 mol %; no less than 25 mol %; no less than 30 mol %; no less than 40 mol %; no less than 50 mol %; no less than 60 mol %; no less than 70 mol %; no less than 75 mol %; no less than 80 mol %; no less than 90 mol %; or no less than 95 mol %.

B. Exemplary Catalyst Materials

Exemplary methods and systems disclosed and contemplated herein may comprise contacting exemplary gas streams with a catalyst material.

Exemplary catalyst materials may include various materials comprising silicon (Si) and aluminum (Al). In some instances, silicon (Si) and aluminum (Al) are present in the compounds silica ($SiO_2$) and alumina ($Al_2O_3$), respectively. In various instances, the silicon (Si) and aluminum (Al) may be present in zeolite-based materials. The term "zeolite," as used herein means a structurally ordered aluminosilicate based on a network of tetrahedra ($TO_4$), where the T atom can either be a silicon or aluminum atom. In various instances, exemplary zeolite-based materials may comprise a zeolite of formula $Na_nAl_nSi_{96-n}O_{192}\cdot 16H_2O$, where n is greater than 0 and less than 27 (also referred to as Zeolite Socony Mobil-5, "ZSM-5").

In various instances, the zeolite-based material may have a silicon (Si) to aluminum (Al) atomic ratio of 11.5 to 300. In some instances, the zeolite-based material may have silicon (Si) to aluminum (Al) atomic ratio of molar ratio of 12 to 280; 15 to 250; 17 to 230; 20 to 200; 25 to 175; to 170; 40 to 160; 50 to 150; 60 to 140; 70 to 130; 80 to 120; or 90 to 110. In some instances, the zeolite-based material may have a silicon (Si) to aluminum (Al) atomic ratio of no greater than 300; no greater than 275; no greater than 250; no greater than 225; no greater than 200; no greater than 175; no greater than 150; no greater than 125; no greater than 100; no greater than 90; no greater than 80; no greater than 70; no greater than 60; no greater than 50; no greater than 45; no greater than 40; no greater than 35; no greater than 30; no greater than 25; no greater than 20; or no greater than 15. In some instances, the zeolite-based material may have a silicon (Si) to aluminum (Al) atomic ratio of no less than 11.5; no less than 12; no less than 15; no less than 20; no less than 25; no less than 30; no less than 35; no less than 40; no less than 45; no less than 50; no less than 60; no less than 70; no less than 80; no less than 90; no less than 100; no less than 125; no less than 150; no less than 175; no less than 200; no less than 225; no less than 250; or no less than 275.

Exemplary zeolite-based materials may have various pore sizes. In various instances, the zeolite-based material may have a pore size of 4 Å to 20 Å. In some instances, the zeolite-based material may have a pore size of 5 Å to 19 Å; 6 Å to 18 Å; 7 Å to 17 Å; 8 Å to 16 Å; 9 Å to 14 Å; 10 Å to 13 Å; or 11 Å to 12 Å. In some instances, the zeolite-based material may have a pore size of no greater than 20 Å; no greater than 18 Å; no greater than 16 Å; no greater than 14 Å; no greater than 12 Å; no greater than 10 Å; no greater than 8 Å; or no greater than 6 Å. In some instances, the zeolite-based material may have a pore size of no less than 4 Å; no less than 6 Å; no less than 8 Å; no less than 10 Å; no less than 12 Å; no less than 14 Å; no less than 16 Å; or no less than 18 Å.

Exemplary catalyst materials may further comprise a transition metal. Exemplary transition metals include, molybdenum (Mo), tungsten (W), zinc (Zn), gallium (Ga), rhenium (Re), iron (Fe), cobalt (Co), copper (Cu), platinum (Pt), rhodium (Rh), and combinations thereof. In various instances, the catalyst material may comprise at least one of molybdenum (Mo), tungsten (W), zinc (Zn), gallium (Ga), rhenium (Re), or iron (Fe). In some instances, the catalyst material may comprise molybdenum (Mo).

In some instances, the catalyst material may comprise molybdenum (Mo) at 2.0% by weight (wt %) to 5.0 wt %. In various instances, the catalyst material may comprise molybdenum (Mo) at 2.2 wt % to 4.8 wt %; 2.4 wt % to 4.6 wt %; 2.6 wt % to 4.4 wt %; 2.8 wt % to 4.2 wt %; 3.0 wt % to 4.0 wt %; 3.2 wt % to 3.8 wt %; or 3.4 wt % to 3.6 wt %. In various instances, the catalyst material may comprise molybdenum (Mo) at no greater than 5.0 wt %; no greater than 4.8 wt %; no greater than 4.6 wt %; no greater than 4.4 wt %; no greater than 4.2 wt %; no greater than 4.0 wt %; no greater than 3.8 wt %; no greater than 3.6 wt %; no greater than 3.4 wt %; no greater than 3.2 wt %; no greater than 3.0 wt %; no greater than 2.8 wt %; no greater than 2.6 wt %; no greater than 2.4 wt %; or no greater than 2.2 wt %. In various instances, the catalyst material may comprise molybdenum (Mo) at no less than 2.0 wt %; no less than 2.2 wt %; no less than 2.4 wt %; no less than 2.6 wt %; no less than 2.8 wt %; no less than 3.0 wt %; no less than 3.2 wt %; no less than 3.4 wt %; no less than 3.6 wt %; no less than 3.8 wt %; no less than 4.0 wt %; no less than 4.2 wt %; no less than 4.4 wt %; no less than 4.6 wt %; or no less than 4.8 wt %.

Exemplary catalyst materials may be prepared according to general methods known to those of in the art. In some instances, solid-state ion exchange methods may be used to prepare catalyst materials comprising zeolite-based materials and transition metals.

C. Exemplary Products

Exemplary fluid products generated by exemplary systems and methods disclosed and contemplated herein may comprise gas products and liquid products. In some instances, reactor effluent may comprise 50% to 80% unreacted reactants, where a remainder comprises various products such as those example products discussed below.

1. Exemplary Aromatic Products

Exemplary products may comprise aromatic products. Exemplary aromatic products may comprise one or more aromatic compounds. In various instances, exemplary aromatic compounds include benzene, toluene, and xylenes. Exemplary xylenes include o-xylene, m-xylene, p-xylene, ethylbenzene, and combinations thereof.

In various instances, exemplary aromatic products may comprise benzene at 30 mol % to 80 mol %. In various instances, exemplary aromatic products may comprise benzene at 30 mol % to 80 mol %; 30 mol % to 55 mol %; 55 mol % to 80 mol %; or 40 mol % to 70 mol %. In various instances, exemplary aromatic products may comprise benzene at no greater than 80 mol %; no greater than 70 mol %; no greater than 60 mol %; no greater than 50 mol %; no greater than 40 mol %; or no greater than 35 mol %. In various instances, exemplary aromatic products may comprise benzene at no less than 30 mol %; no less than 40 mol %; no less than 50 mol %; no less than 60 mol %; no less than 70 mol %; or no less than 75 mol %.

In various instances, the aromatic products may comprise toluene at 1 mol % to 23 mol %. In various instances, exemplary aromatic products may comprise toluene at 1 mol % to 11 mol %; 11 mol % to 23 mol %; 4 mol % to 20 mol %; or 8 mol % to 16 mol %. In various instances, exemplary aromatic products may comprise toluene at no greater than 23 mol %; no greater than 20 mol %; no greater than 17 mol %; no greater than 14 mol %; no greater than 11 mol %; no greater than 8 mol %; no greater than 5 mol %; or no greater than 2 mol %. In various instances, exemplary aromatic products may comprise toluene at no less than 1 mol %; no less than 4 mol %; no less than 7 mol %; no less than 10 mol %; no less than 13 mol %; no less than 16 mol %; or no less than 19 mol %.

In various instances, the aromatic products may comprise xylenes at 1 mol % to 47 mol %. In various instances, exemplary aromatic products may comprise xylenes at 1 mol % to 47 mol %; 1 mol % to 24 mol %; 24 mol % to 47 mol %; 10 mol % to 40 mol %; or 20 mol % to 30 mol %. In various instances, exemplary aromatic products may comprise xylenes at no greater than 47 mol %; no greater than 42 mol %; no greater than 37 mol %; no greater than 32 mol %; no greater than 27 mol %; no greater than 22 mol %; no greater than 17 mol %; no greater than 12 mol %; no greater than 7 mol %; or no greater than 2 mol %. In various instances, exemplary aromatic products may comprise xylenes at no less than 1 mol %; no less than 6 mol %; no less than 11 mol %; no less than 16 mol %; no less than 21 mol %; no less than 26 mol %; no less than 31 mol %; no less than 36 mol %; no less than 41 mol %; or no less than 46 mol %.

2. Exemplary Alkene Products

In various instances, exemplary products may comprise alkene products. Exemplary alkene products may comprise one or more $C_{2-4}$alkenes. Exemplary $C_{2-4}$ alkenes may include ethene, propene, 1-butene, isobutene, cis-2-butene, trans-2-butene, and 1,3-butadiene.

III. EXEMPLARY SYSTEMS

Various systems may be used to perform exemplary methods and techniques described herein. FIG. 1 is a schematic illustration of exemplary gas stream processing system 100. Broadly, gas stream processing system 100 is configured to process a gas stream and generate fluid products. As shown, gas stream processing system 100 includes a gas source 102, a reactor 104, a voltage supply and monitor system 200, and a collection vessel 110. Various optional components are shown in dotted outline. Various electrical connections are shown in dashed lines. Other embodiments may include more or fewer components.

A. Exemplary Reactors

Reactor 104 may be configured to receive and process a gas stream from gas source 102. In the embodiment shown, reactor 104 is arranged vertically, such that material enters near a top portion of reactor 104, flows downward, and exits near a bottom portion of reactor 104.

Reactor 104 may include a first reactor inlet 112 configured to receive one or more fluids, such as a gas stream, from a gas source 102. In some instances, reactor 104 may further include a second rector inlet 124 configured to receive one or more fluids, such as nitrogen ($N_2$) gas from a nitrogen ($N_2$) gas source 122. The first reactor inlet 112 and the second reactor inlet 124 may be positioned at an upper portion of the reactor 104.

The reactor 104 may include a "reaction zone" comprising a catalyst material, an inner electrode 114, an outer electrode 116, and an inner volume defined between the inner electrode 114 and the outer electrode 116. In some instances, the reaction zone may extend through a portion of the interior of the reactor 104. In some instances, the reaction zone may extend through the interior of the reactor 104.

In various instances, the reaction zone 104 may comprise catalyst material arranged as a catalyst bed 108. The catalyst bed 108 may be a fixed bed. In some instances, the catalyst material of catalyst bed 108 may be in the form of particles. Exemplary catalyst material particles may be spherical or semi-spherical.

The size of the catalyst material particles may vary based on the reactor type. In various instances, exemplary catalyst material particles may have an average diameter of 150 μm to 250 μm. In various instances, the catalyst particles may have an average diameter of 150 μm to 200 μm; 200 μm to 250 μm; 180 μm to 220 μm; or 190 μm to 210 μm. In various instances, the catalyst particles may have an average diameter of no greater than 250 μm; no greater than 225 μm; no greater than 200 μm; no greater than 175 μm; no greater than 160 μm. In various instances, the catalyst particles may have an average diameter of no less than 150 μm; no less than 175 μm; no less than 200 μm; no less than 225 μm; or no less than 240 μm.

In various instances, the catalyst bed 108 may occupy one half to three-fourths, or one half to two-thirds, of a volume of the reaction zone 104. In some instances, the catalyst bed 108 may occupy no greater than three-fourths, no greater than two-thirds, or no greater than one half of the reaction zone 104. In some instances, the catalyst bed 108 may occupy no less than one half; or no less than two-thirds of the reaction zone 104.

The catalyst material may be provided at various packing densities. In various instances, the catalyst bed 108 may have a packing density of 0.43 g/mL to 0.05 g/mL. In various instances, the catalyst bed 108 may have a packing density of 0.05 g/mL to 0.40 g/mL; 0.05 g/mL to 0.2 g/mL;

0.2 g/mL to 0.4 g/mL or 0.15 g/mL to 0.35 g/mL. In various instances, the catalyst bed 108 may have a packing density of no greater than 0.43 g/mL; no greater than 0.38 g/mL; no greater than 0.33 g/mL; no greater than 0.28 g/mL; no greater than 0.23 g/mL; no greater than 0.18 g/mL; no greater than 0.13 g/mL; or no greater than 0.08 g/mL. In various instances, the catalyst bed 108 may have a packing density of no less than 0.05 g/mL; no less than 0.10 g/mL; no less than 0.15 g/mL; no less than 0.20 g/mL; no less than 0.25 g/mL; no less than 0.3 g/mL; no less than 0.35 g/mL; or no less than 0.40 g/mL.

During typical operation, inner electrode 114 and outer electrode 116 cooperate to generate a plasma in the reaction zone. The plasma may be a non-thermal plasma. During typical operation, the plasma may pass through at least a portion of the catalyst bed 108.

In some instances, the inner electrode 114 may extend through a portion of the interior of reactor 104. In some instances, the inner electrode 114 may extend through the entire interior of reactor 104. In some instances, the reaction zone may be cylindrical, wherein the outer electrode 116 annularly defines the exterior of the reaction zone.

Exemplary inner electrode 114 may comprise various materials. The particular material(s) for the inner electrode 114 may depend on the specific gas processing system. Exemplary materials for inner electrode 114, may include metals such as tungsten, nickel, and stainless steel.

Exemplary outer electrode 116 may comprise various materials. The particular material(s) for the outer electrode 116 may depend on the specific gas processing system. Exemplary materials for outer electrode 116, may include metals such as stainless steel and copper.

Inner electrode 114 and outer electrode 116 may be in electrical communication with a voltage supply and monitor system 200. In some instances, the voltage supply and monitor system 200 may be configured to provide a voltage to the inner electrode 114, thereby generating a plasma across a discharge gap 118.

A discharge gap 118 is defined as a distance between the inner electrode 114 and the outer electrode 116, where the distance is normal to both surfaces. A size of the discharge gap 118 may vary depending upon the specific implementation. The specific discharge gap size may influence the breakdown voltage of the plasma. Exemplary reaction zones may have a discharge gap of 0.1 mm to 150 mm. In some instances, exemplary reaction zones may have a discharge gap of 0.15 m to 150 mm; 0.25 mm to 125 mm; 0.50 mm to 100 mm; 1 mm to 99 mm; 2 mm to 98 mm; 5 mm to 95 mm; 8 mm to 92 mm; 10 mm to 90 mm; 12 mm to 88 mm; 15 mm to 85 mm; 18 mm to 82 mm; 20 mm to 80 mm; 22 mm to 78 mm; 25 mm to 75 mm; 28 mm to 72 mm; 30 mm to 70 mm; 32 mm to 68 mm; 35 mm to 65 mm; 38 mm to 62 mm; 40 mm to 60 mm; 42 mm to 58 mm; 45 mm to 55 mm; or 48 mm to 52 mm. In various instances, exemplary reaction zones may have a discharge gap of no greater than 150 mm; no greater than 125 mm; no greater than 100 mm; no greater than 90 mm; no greater than 80 mm; no greater than 75 mm; no greater than 70 mm; no greater than 60 mm; no greater than 50 mm; no greater than 40 mm; no greater than 30 mm; no greater than 25 mm; no greater than 20 mm; no greater than 15 mm; no greater than 10 mm; no greater than 5 mm; no greater than 1 mm; or no greater than 0.5 mm. In various instances, exemplary reaction zones may have a discharge gap of no less than 0.1 mm; no less than 0.25 mm; no less than 0.5 mm; no less than 1 mm; no less than 5 mm; no less than 10 mm; no less than 15 mm; no less than 20 mm; no less than 25 mm; no less than 30 mm; no less than 40 mm; no less than 50 mm; no less than 60 mm; no less than 70 mm; no less than 75 mm; no less than 80 mm; no less than 90 mm; no less than 100 mm; or no less than 125.

In some implementations, reactor 104 may further include a reactor temperature regulation unit 126. Exemplary reactor temperature regulation unit 126 may be arranged to maintain a predetermined temperature within the reactor. For instance, the reactor temperature regulation unit 126 may be configured to maintain a predetermined reaction zone temperature. The reactor temperature regulation unit 126 may be positioned around an exterior portion of the reactor 104. Various components known in the art for temperature control may be used for reactor temperature regulation unit 126. In various instances, exemplary reactor temperature regulation components 126 may maintain a reaction zone temperature of from 300° C. to 700° C.

Reactor 104 may further comprise a reactor outlet 120. Reactor outlet 120 may be positioned at a lower portion of the reactor. In various instances, the reactor outlet 120 may be configured to provide one or more fluid products, such as liquid products, to a collection vessel 110.

Exemplary collection vessels 110 may comprise exemplary materials, such as stainless steel, carbon steel, glass, quartz, and combinations thereof. Exemplary collection vessels 110 may vary depending on the product's composition and volume. In various instances, exemplary collection vessels 110 may be air-free. For example, in some instances, exemplary collection vessels may be maintained under argon (Ar) or nitrogen ($N_2$) atmosphere.

In some instances, the reactor outlet 120 may be configured to provide one or more fluid products, such as liquid products, to an analysis unit 128 for product analysis. In various instances, the analysis unit 128 may be a mass spectrometer and/or a gas chromatograph (GC). Exemplary detectors for the gas chromatograph may comprise one or more of: a thermal conductivity detector (TCD), a flame ionization detector (FID), and a photoionization detector (PID). Specific configurations of analysis unit 128 may vary depending on the implementation.

In some instances, the reactor 104 may be configured to recycle unreacted gases from the reactor back to the first reactor inlet 112 via a fluid pathway 130.

B. Exemplary Gas Stream Sources

Exemplary gas source 102 may be any suitable reservoir containing gas. In various instances, gas source 102 may include various components configured to provide a gas stream from a reservoir containing gas to the first reactor inlet.

C. Exemplary Voltage Supply and Monitor Systems

Voltage supply and monitor system 200 provides voltage to inner electrode 114 and monitors voltage from outer electrode 116. Various exemplary components of voltage supply and monitor system are shown in FIG. 2, discussed below.

Figure 2:
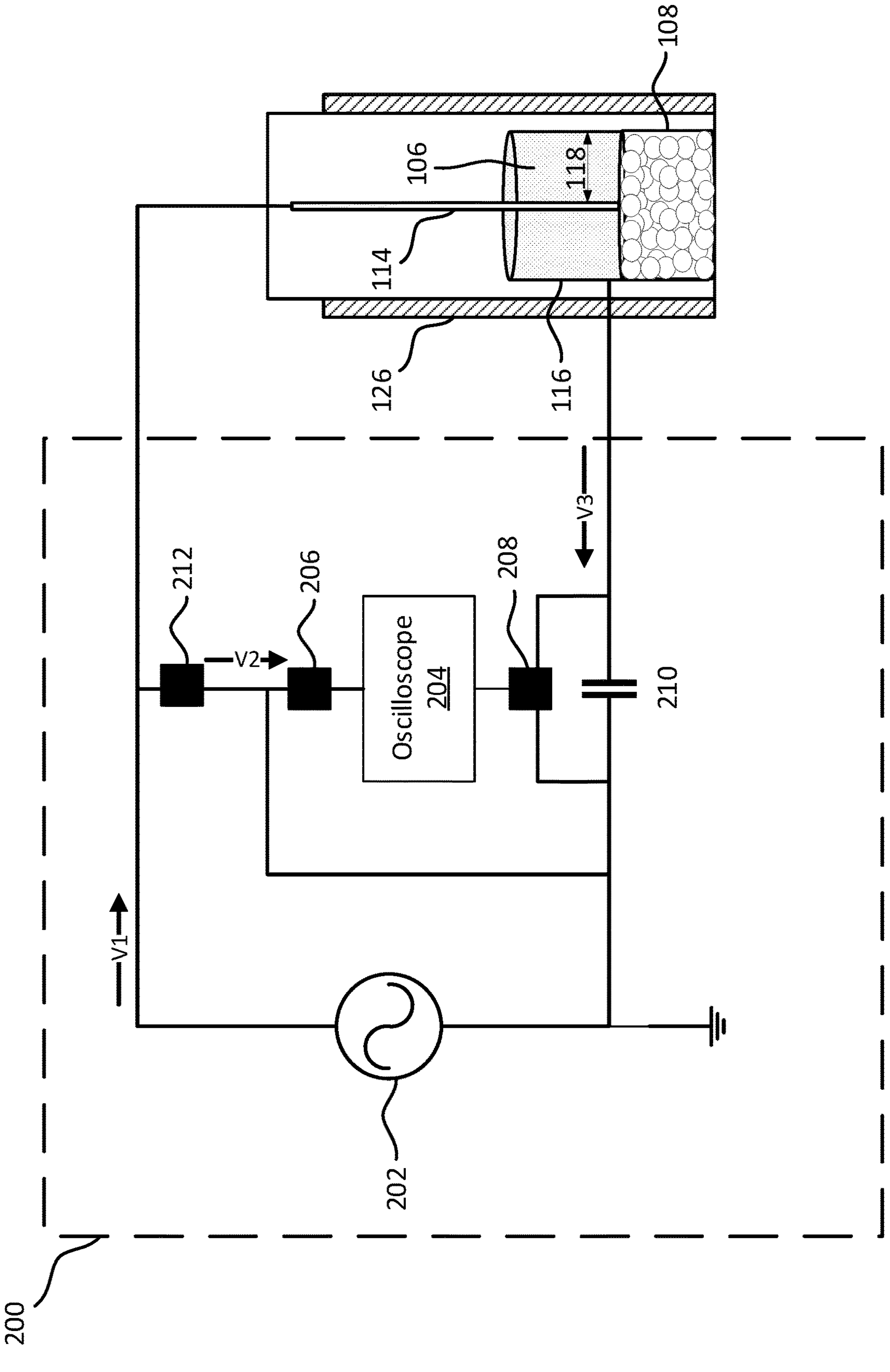
FIG. 2 is a schematic depiction of an exemplary voltage supply and monitor system for exemplary systems for processing gas streams.

As shown in FIG. 2, exemplary voltage supply and monitor system 200 may comprise a power source 202, an oscilloscope 204, probes 206, 208, a capacitor 210, and a voltage attenuator 212. Other embodiments may include more or fewer components.

Exemplary power source 202 provides a voltage V1 to inner electrode 114. Typically, exemplary power source 202 is an alternating current (A/C) power source. Exemplary power source 202 may be adjustable. In some instances, exemplary power source 202 may provide power intermittently, such as in pulses provided in a given time interval. In some instances, an exemplary interval may be every 1 second; every 2 seconds; every 5 seconds; every 10 seconds;

every 15 seconds; every 20 seconds; every 30 seconds; every 45 seconds; every 60 seconds; every 90 seconds; every 120 seconds, or another interval.

In some implementations, the power source 202 is connected to a voltage attenuator 212. The voltage attenuator 212 decreases the first voltage V1 that is output from the power source 202. In various instances, the voltage attenuator 212 attenuates the voltage to a predetermined input: output ratio. As discussed in greater detail below, an exemplary input:output attenuation ratio may be 1000:1.

In some implementations, the oscilloscope 204 determines voltage waveforms with each probe 206, 208. The probes 206, 208 extend from the oscilloscope 204. For example, a first probe 206 may extend from a first channel of the oscilloscope 204 and a second probe 208 may extend from a second channel of the oscilloscope 204. In some implementations, the second probe 208 is also connected to a grounding source. In some implementations, the first probe 206 is connected to the voltage attenuator 212 that attenuates the first voltage V1 that is output from the power source 202.

A second voltage V2 (i.e., the attenuated voltage) may be provided to the oscilloscope 204 by the first probe 206. In some instances, the second voltage V2 has the same frequency as the first voltage V1. In some instances, the voltage that is not output (i.e., the difference between the first voltage V1 and the second voltage V2) is sent to ground.

The oscilloscope 204 may measure a third voltage V3 across the capacitor 210 with the second probe 208. In some implementations, the capacitor 210 has a capacitance of 10 nano Farads (nF). In some instances, the capacitor's capacitance may be provided to the reactor's capacitance. In various instances, the ratio of the capacitor's capacitance to the reactor's capacitance may be 100:1 to 10,000:1. In some instances, the ratio of the capacitor's capacitance to the reactor's capacitance may be 100:1 to 9,000:1; 200:1 to 8,000:1; 300:1 to 7,000:1; 400:1 to 6,000:1; 500:1 to 5,000:1; 600:1 to 4,000:1; 700:1 to 3,000:1; to 800:1 to 2,000:1; or 900:1 to 1,000:1. In some instances, the ratio of the capacitor's capacitance to the reactor's capacitance may be no greater than 10,000:1; no greater than 9,000:1; no greater than 8,000:1; no greater than 7,000:1; no greater than 6,000:1; no greater than 5,000:1; no greater than 4,000:1; no greater than 3,000:1; no greater than 2,000:1; no greater than 1,000:1, no greater than 900:1; no greater than 800:1; no greater than 700:1; no greater than 600:1; no greater than 500:1; no greater than 400:1; no greater than 300:1; or no greater than 200:1. In some instances, the ratio of the capacitor's capacitance to the reactor's capacitance may be no less than 100:1; no less than 200:1; no less than 300:1; no less than 400:1; no less than 500:1; no less than 600:1; no less than 700:1; no less than 800:1; no less than 900:1; no less than 1,000:1; no less than 2,000:1; no less than 3,000:1; no less than 4,000:1; no less than no less than 6,000:1; no less than 7,000:1; no less than 8,000:1; or no less than 9,000:1.

The third voltage V3 is voltage output from the outer electrode 116. In some implementations, the oscilloscope 204 determines a relationship between the second voltage V2 and the third voltage V3 to determine a power of a plasma that is generated in a reaction zone of the reactor.

IV. EXEMPLARY METHODS

Figure 3:
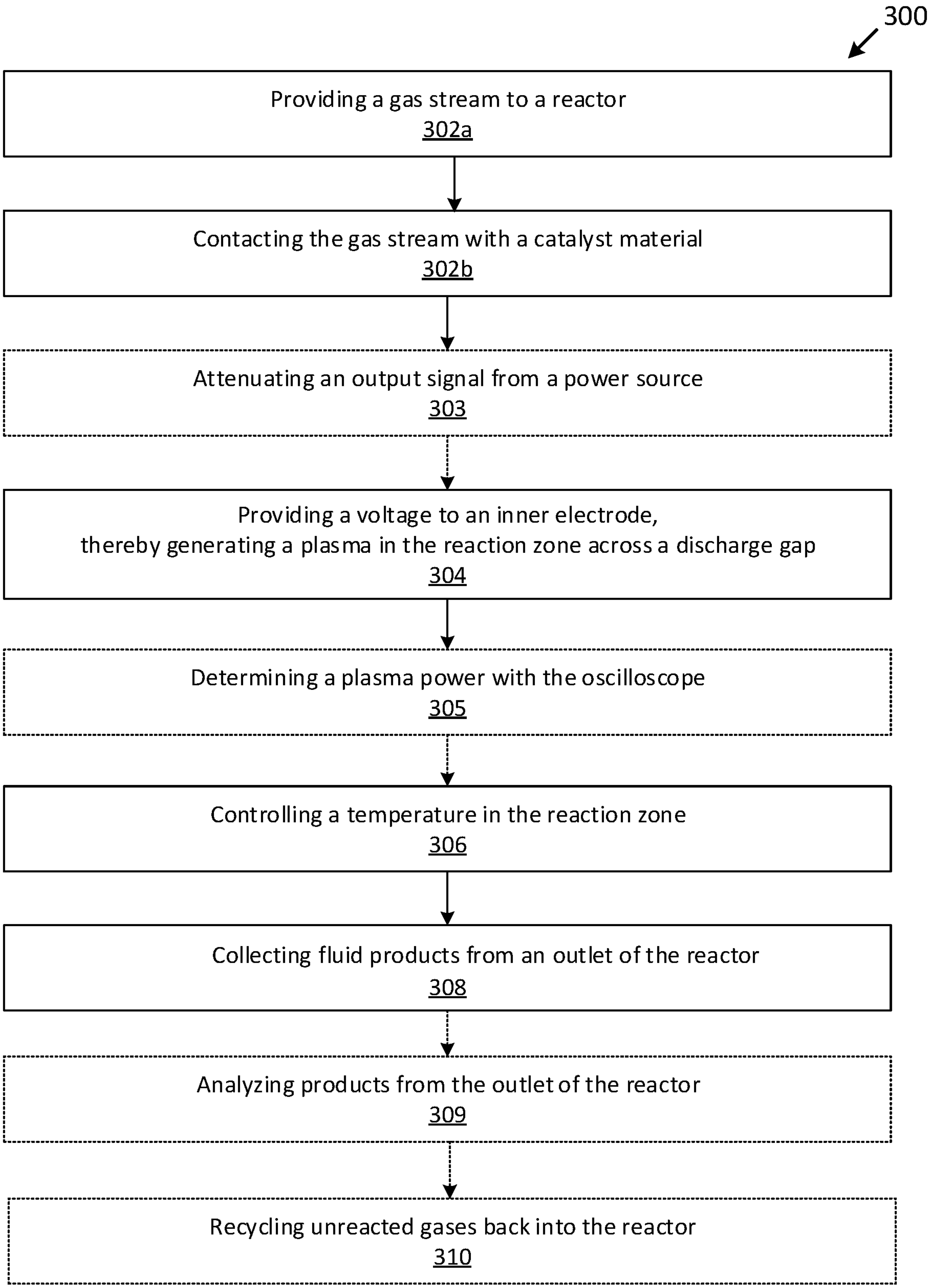
FIG. 3 shows a flowchart of an exemplary method for processing a gas stream.
Figure 4:
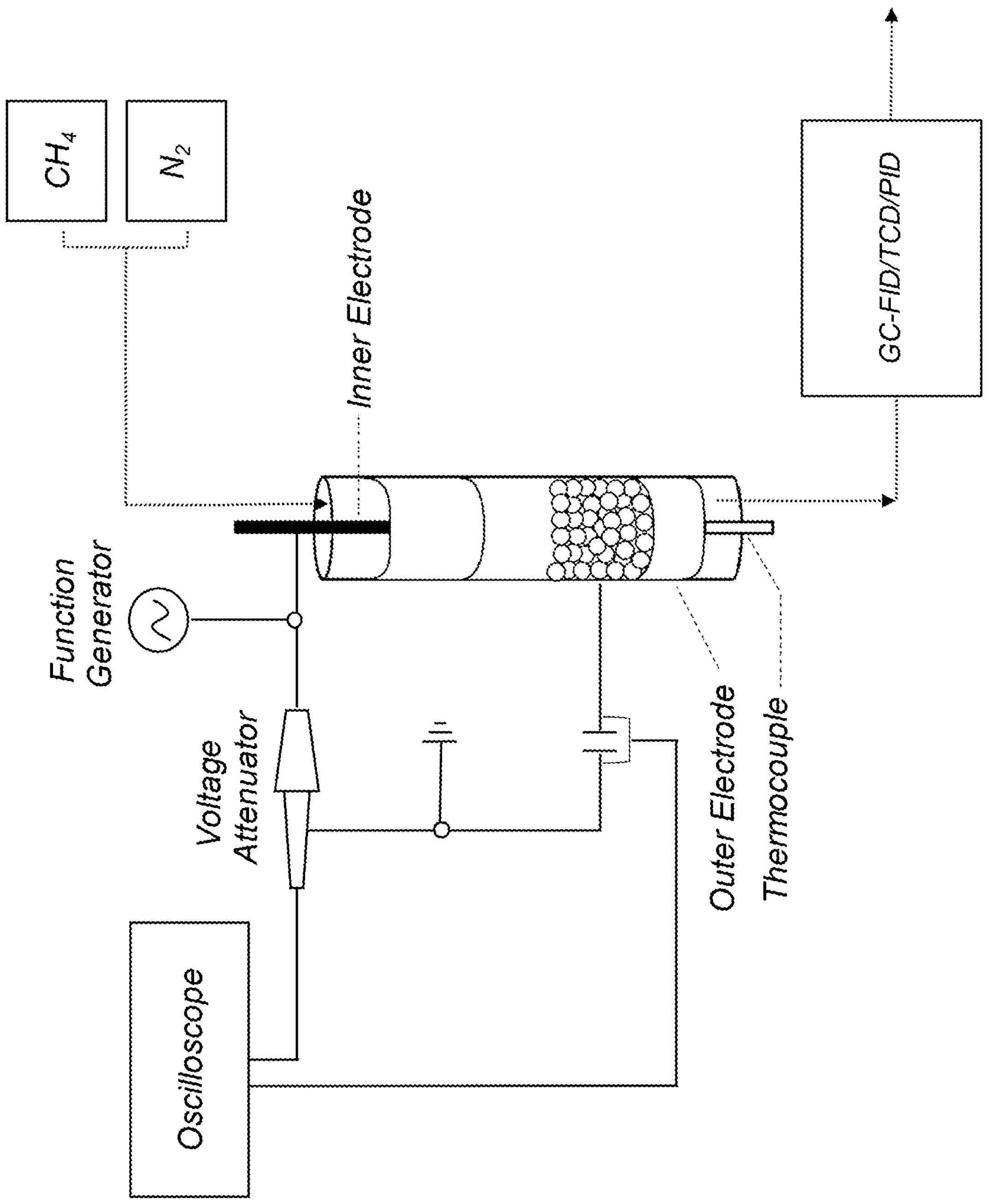
FIG. 4 depicts an exemplary dielectric barrier discharge reactor system with a gas chromatograph (GC).

Exemplary methods for processing gas streams disclosed and contemplated herein include one or more operations. FIG. 3 is a schematic illustration of exemplary method 300 for processing a gas stream. Broadly, method 300 includes providing a gas stream to a reactor (operation 302*a*), contacting the gas stream with a catalyst material (operation 302*b*), providing a voltage (e.g., first voltage V1) to an inner electrode disposed within a reaction zone of the reactor, thereby generating a plasma in the reaction zone across a discharge gap (operation 304), controlling a temperature in the reaction zone (operation 306), and collecting fluid products from an outlet of the reactor (operation 308). Various optional operations are shown in dotted outline in FIG. 3. Other embodiments may include more or fewer operations.

A. Providing a Gas Stream to a Reactor

In various instances, providing the gas stream to the reactor (operation 302*a*) comprises providing a gas stream comprising methane at a first flowrate to a first inlet of the reactor.

In various instances, the first flowrate may be 5 standard cubic centimeters per minute (SCCM) ($cm^3$/min) to 11,304 $cm^3$/min. In some instances, the first flowrate is 10 $cm^3$/min to 11,000 $cm^3$/min; 20 $cm^3$/min to 10,000 $cm^3$/min; 30 $cm^3$/min to 9,000 $cm^3$/min; 40 $cm^3$/min to 8,000 $cm^3$/min; 50 $cm^3$/min to 7,000 $cm^3$/min; 60 $cm^3$/min to 6,000 $cm^3$/min; 70 $cm^3$/min to 5,000 $cm^3$/min; 80 $cm^3$/min to 4,000 $cm^3$/min; 90 $cm^3$/min to 3,000 $cm^3$/min; 100 $cm^3$/min to 2,000 $cm^3$/min; 200 $cm^3$/min to 1,000 $cm^3$/min; 300 $cm^3$/min to 900 $cm^3$/min; 400 $cm^3$/min to 800 $cm^3$/min; or 500 $cm^3$/min to 700 $cm^3$/min. In various instances, the first flowrate may be no greater than 11,304 $cm^3$/min; no greater than 11,000 $cm^3$/min; no greater than 10,000 $cm^3$/min; no greater than 9,000 $cm^3$/min; no greater than 8,000 $cm^3$/min; no greater than 7,000 $cm^3$/min; no greater than 6,000 $cm^3$/min; no greater than 5,000 $cm^3$/min; no greater than 4,000 $cm^3$/min; no greater than 3,000 $cm^3$/min; no greater than 2,000 $cm^3$/min; no greater than 1,000 $cm^3$/min; no greater than 900 $cm^3$/min; no greater than 800 $cm^3$/min; no greater than 700 $cm^3$/min; no greater than 600 $cm^3$/min; no greater than 500 $cm^3$/min; no greater than 400 $cm^3$/min; no greater than 300 $cm^3$/min; no greater than 200 $cm^3$/min; no greater than 100 $cm^3$/min; no greater than 90 $cm^3$/min; no greater than 80 $cm^3$/min; no greater than 70 $cm^3$/min; no greater than 60 $cm^3$/min; no greater than 50 $cm^3$/min; no greater than 40 $cm^3$/rain; no greater than 30 $cm^3$/min; no greater than 20 $cm^3$/min; or no greater than 10 $cm^3$/min. In various instances, the first flowrate may be no less than 5 $cm^3$/min; no less than 10 $cm^3$/min; no less than 20 $cm^3$/min; no less than 30 $cm^3$/min; no less than 40 $cm^3$/min; no less than 50 $cm^3$/min; no less than 60 $cm^3$/min; no less than 70 $cm^3$/min; no less than 80 $cm^3$/min; no less than 90 $cm^3$/min; no less than 100 $cm^3$/min; no less than 200 $cm^3$/min; no less than 300 $cm^3$/min; no less than 400 $cm^3$/min; no less than 500 $cm^3$/min; no less than 600 $cm^3$/min; no less than 700 $cm^3$/min; no less than 800 $cm^3$/min; no less than 900 call/min; no less than 1,000 $cm^3$/min; no less than 2,000 $cm^3$/min; no less than 3,000 cm/min; no less than 4,000 $cm^3$/min; no less than 5,000 $cm^3$/min; no less than 6,000 $cm^3$/min; no less than 7,000 $cm^3$/min; no less than 8.000 $cm^3$/min; no less than 9.000 $cm^3$/min; no less than 10,000 $cm^3$/min; or no less than 11.000 $cm^3$/min.

Method 300 may further comprise providing nitrogen ($N_2$) gas at a second flowrate to a second inlet of the reactor.

In various instances, the second flowrate may be 4 $cm^3$/min to 10,174 $cm^3$/min. In some instances, the second flowrate may be 10 $cm^3$/min to 10,000 $cm^3$/min; 20 $cm^3$/min to 9,000 $cm^3$/min; 30 $cm^3$/min to 8,000 $cm^3$/min; 40 $cm^3$/min to 7,000 $cm^3$/min; 50 $cm^3$/min to 6,000 $cm^3$/min; 60 $cm^3$/min to 5,000 $cm^3$/min; 70 $cm^3$/min to 4,000 $cm^3$/min; 80 $cm^3$/min to 3,000 $cm^3$/min; 90 $cm^3$/min to 2,000 $cm^3$/min; 100 $cm^3$/min to 1,000 $cm^3$/min; 200 $cm^3$/min to 900

$cm^3$/min; 300 $cm^3$/min to 800 $cm^3$/min, 400 $cm^3$/min to 700 $cm^3$/min; or 500 $cm^3$/min to 600 $cm^3$/min. In various instances, the second flowrate may be no greater than 10,174 $cm^3$/min; no greater than 10,000 $cm^3$/min; no greater than 9,000 $cm^3$/min; no greater than 8,000 $cm^3$/min; no greater than 7,000 $cm^3$/min; no greater than 6,000 $cm^3$/min; no greater than 5,000 $cm^3$/min; no greater than 4,000 $cm^3$/min; no greater than 3,000 $cm^3$/min; no greater than 2,000 $cm^3$/grin; no greater than 1,000 $cm^3$/min; no greater than 900 $cm^3$/min; no greater than 800 $cm^3$/min; no greater than 700 $cm^3$/min; no greater than 600 $cm^3$/min; no greater than 500 $cm^3$/min; no greater than 400 $cm^3$/grin; no greater than 300 $cm^3$/min; no greater than 200 $cm^3$/min; no greater than 100 $cm^3$/min; no greater than 90 $cm^3$/min; no greater than 80 $cm^3$/min; no greater than 70 $cm^3$/min; no greater than 60 $cm^3$/min; no greater than 50 $cm^3$/min; no greater than 40 $cm^3$/min; no greater than 30 $cm^3$/min; no greater than 20 $cm^3$/rain; or no greater than 10 $cm^3$/min. In various instances, the second flowrate may be no less than 4 $cm^3$/min; no less than 10 $cm^3$/min; no less than 20 $cm^3$/min; no less than 30 $cm^3$/min; no less than 40 $cm^3$/min; no less than 50 $cm^3$/min; no less than 60 $cm^3$/min; no less than 70 $cm^3$/min; no less than 80 $cm^3$/min; no less than 90 $cm^3$/min; no less than 100 $cm^3$/min; no less than 200 $cm^3$/min; no less than 300 $cm^3$/min; no less than 400 $cm^3$/min; no less than 500 $cm^3$/min; no less than 600 $cm^3$/min; no less than 700 $cm^3$/min; no less than 800 $cm^3$/min; no less than 900 $cm^3$/min; no less than 1,000 $cm^3$/min; no less than 2,000 $cm^2$/min; no less than 3,000 $cm^3$/min, no less than 4,000 $cm^3$/min; no less than 5,000 $cm^3$/min, no less than 6,000 $cm^3$/min; no less than 7,000 $cm^3$/min, no less than 8,000 $cm^3$/min; no less than 9,000 $cm^3$/min; or no less than 10,000 $cm^3$/min.

B. Contacting Gas Stream with Catalyst Material

Exemplary method 300 may further comprise contacting the gas stream with a catalyst material (operation 302*b*). In various instances, contacting the gas stream with a catalyst material may comprise flowing the gas stream downward from a top portion of the reactor into a reaction zone comprising catalyst material (e.g., reaction zone 104). As the input stream flows downward, the gas stream may contact a surface of a catalyst bed comprising the catalyst material (e.g., catalyst bed 108).

C. Providing a Voltage to Inner Electrode

Exemplary method 300 may further comprise providing a voltage (e.g., first voltage V1) to an inner electrode disposed within a reaction zone of the reactor, thereby generating a plasma in the reaction zone across a discharge gap (operation 304). The plasma generated in the reaction zone may be a non-thermal plasma. Exemplary voltages may be provided from a power source, such as power source 202.

In various instances, the voltage provided to the inner electrode may be 6.0 kV to 9.0 kV. In some instances, the voltage provided to the inner electrode may be 6.5 kV to 9.0 kV; 7.0 kV to 8.5 kV; 7.5 kV to 8.5 kV; 7.6 kV to 8.4 kV; 7.7 kV to 8.3 kV; 7.8 kV to 8.2 kV; or 7.9 kV to 8.1 kV. In various instances, the voltage provided to the inner electrode may be no greater than 9.0 kV; no greater than 8.5 kV; no greater than 8.4 kV; no greater than 8.3 kV; no greater than 8.2 kV; no greater than 8.1 kV; no greater than 8.0 kV; no greater than 7.9 kV; no greater than 7.8 kV; no greater than 7.7 kV; or no greater than 7.6 kV. In various instances, the voltage provided to the inner electrode may be no less than 6; no less than 6.5 kV; no less than 7.0 kV; no less than 7.5 kV; no less than 7.6 kV; no less than 7.7 kV; no less than 7.8 kV; no less than 7.9 kV; no less than 8.0 kV; no less than 8.1 kV; no less than 8.2 kV; no less than 8.3 kV; no less than 8.4 kV; or no less than 8.5 kV.

In various instances, the voltage may be provided to the inner electrode at a frequency of 2 kHz to 700 kHz. In some instances, the voltage may be provided to the inner electrode at a frequency of 5 kHz to 675 kHz; 10 kHz to 650 kHz; 15 kHz to 625 kHz; 20 kHz to 600 kHz; 25 kHz to 575 kHz; 30 kHz to 550 kHz; 35 kHz to 525 kHz; 40 kHz to 500 kHz; 45 kHz to 475 kHz; 50 kHz to 450 kHz; 55 kHz to 425 kHz; 60 kHz to 400 kHz; 65 kHz to 375 kHz; 70 kHz to 350 kHz; 75 kHz to 325 kHz; 80 kHz to 300 kHz; 85 kHz to 275 kHz; 90 kHz to 250 kHz; 95 kHz to 225 kHz; 100 kHz to 200 kHz; or 125 kHz to 175 kHz. In some instances, the voltage may be provided to the inner electrode at a frequency of no greater than 700 kHz; no greater than 650 Hz; no greater than 600 kHz; no greater than 550 kHz; no greater than 500 kHz; no greater than 450 kHz; no greater than 400 kHz; no greater than 350 kHz; no greater than 300 kHz; no greater than 250 kHz; no greater than 200 kHz; no greater than 150 kHz; no greater than 100 kHz; no greater than 50 kHz; no greater than 25 kHz; no greater than 20 kHz; no greater than 15 kHz; no greater than 10 kHz; or no greater than 5 kHz. In some instances, the voltage may be provided to the inner electrode at a frequency of no less than 5 kHz; no less than 10 kHz; no less than 15 kHz; no less than 20 kHz; no less than 25 kHz; no less than 50 kHz; no less than 100 kHz; no less than 150 kHz; no less than 200 kHz; no less than 250 kHz; no less than 300 kHz; no less than 350 kHz; no less than 400 kHz; no less than 450 kHz; no less than 500 kHz; no less than 550 kHz; no less than 600 kHz; or no less than 650 kHz.

In some instances, method 300 may comprise attenuating an output signal from the power source (operation 303). For example, in some instances the output signal may be attenuated to an input:output ratio of 1000:1. In some instances, method 300 may further comprise providing the attenuated output signal to an oscilloscope (e.g., oscilloscope 204). In some instances, method 300 may further comprise determining a plasma power input with the oscilloscope (operation 305).

In various instances, the plasma power input may be 9 watts (W) to 11 W. In some instances, the plasma power input may be 9.1 W to 10.9 W; 9.2 W to 10.8 W; 9.3 W to 10.7 W; 9.4 W to 10.6 W; 9.5 W to 10.5 W; 9.6 W to 10.4 W; 9.7 W to 10.3 W; 9.8 W to 10.2 W; or 9.9 W to 10.1 W. In some instances, the plasma power input may be no greater than 11 W; no greater than 10.75 W; no greater than 10.5 W; no greater than 10.25 W; no greater than 10 W; no greater than 9.75 W; no greater than 9.5 W; no greater than 9.25 W; or no greater than 9.2 W. In some instances, the plasma power input may be no less than 9 W; no less than 9.25 W; no less than 9.5 W; no less than 9.75 W; no less than 10 W; no less than 10.25 W; no less than 10.5 W; no less than 10.75 W; or no less than 10.8 W.

In various instances, the specific energy input (SEI) to the reaction zone can be determined. Specific energy input (SEI) is the ratio of the calculated plasma power to the gas flow rate. As described above, in various instances, an oscilloscope (e.g., oscilloscope 204) may calculate the power of the plasma that is generated in a reaction zone from a relationship between the second voltage V2 (e.g., attenuated input voltage V2, measured with probe 206) and the third voltage V3 (e.g., output voltage V3 from the outer electrode 116, measured across the capacitor 210 with the second probe 208).

In various instances, the specific energy input may be from 1 kJ/L to 100 kJ/L. In some instances, the specific energy input may be from 1 kJ/L to 99 kJ/L; 5 kJ/L to 95 kJ/L; 10 kJ/L to 90 kJ/L; 15 kJ/L to 85 kJ/L; 20 kJ/L to 80 kJ/L; 25 kJ/L to 75 kJ/L; 30 kJ to 70 kJ/L; 35 kJ/L to 65 kJ/L; 40 kJ/L to 60 kJ/L; 9 kJ/L to 15 kJ/L; or 45 kJ/L to 55 kJ/L. In some instances, the specific energy input may be from no greater than 100 kJ/L; no greater than 90 kJ/L; no greater than 80 kJ/L; no greater than 70 kJ/L; no greater than 60 kJ/L; no greater than 50 kJ/L; no greater than 40 kJ/L; no greater than 35 kJ/L; no greater than 30 kJ/L; no greater than 25 kJ/L; no greater than 20 kJ/L; no greater than 15 kJ/L; no greater than 10 kJ/L; or no greater than 5 kJ/L. In some instances, the specific energy input may be from no less than 5 kJ/L; no less than 10 kJ/L; no less than 15 kJ/L; no less than 20 kJ/L; no less than 25 kJ/L; no less than 30 kJ/L; no less than 40 kJ/L; no less than 50 kJ/L; no less than 60 kJ/L; no less than 70 kJ/L; no less than 80 kJ/L; no less than 90 kJ/L; or no less than 95 kJ/L.

D. Controlling Reaction Zone Temperature

Exemplary method 300 may further comprise controlling the reaction zone's temperature (operation 307). In various instances, the reaction zone may be maintained at a temperature of 300° C. to 700° C. In various instances, the reaction zone may be maintained at a temperature of 325° C. to 675° C.; 350° C. to 650° C.; 375° C. to 625° C.; 300° C. to 500° C.; 400° C. to 600° C.; 425° C. to 575° C.; 450° C. to 550° C.; or 475° C. to 525° C. In various instances, the reaction zone may be maintained at a temperature of no greater than 700° C.; no greater than 675° C.; no greater than 650° C.; no greater than 625° C.; no greater than 600° C.; no greater than 575° C.; no greater than 550° C.; no greater than 525° C.; no greater than 500° C.; no greater than 475° C.; no greater than 450° C.; no greater than 425° C.; no greater than 400° C.; no greater than 375° C.; no greater than 350° C.; or no greater than 325° C. In various instances, the reaction zone may be maintained at a temperature of no less than 300° C.; no less than 325° C.; no less than 350° C.; no less than 375° C.; no less than 400° C.; no less than 425° C.; no less than 450° C.; no less than 475° C.; no less than 500° C.; no less than 525° C.; no less than 550° C.; no less than 575° C.; no less than 600° C.; no less than 625° C.; no less than 650° C.; or no less than 675° C.

E. Collecting Products and Recycling Unreacted Gases

Exemplary method 300 may further comprise collecting fluid products from the reactor outlet (operation 308). In some instances, collecting fluid products (operation 308) may include cooling fluid products from the reactor outlet to generate liquid products.

In some instances, exemplary method 300 may comprise sending fluid products from the reactor outlet to an analysis unit, such as analysis unit 128, where the fluid products may be analyzed (operation 309). In various instances, exemplary analysis unit 128 may provide output data regarding reactant conversion, product types, and product selectivity. In response to the output data from analysis unit 128, various process inputs, such as flow rate, power, compositions, and temperature may be adjusted. Such adjustments in response to output data from analysis unit 128, may improve the processes' reactant conversions and production rates.

In various instances, at least 1% of gases in gas stream may be converted to products. For example, after processing gas streams comprising methane ($CH_4$), 1% to 100% of the methane ($CH_4$) in the gas stream provided to the reactor may be converted to products. In some instances, 1% to 99%; 5% to 95%; 10% to 90%; 15% to 85%; 16% to 84%; 17% to 83%; 18% to 82%; 20% to 80%; 25% to 75%; 30% to 70%; 35% to 65%; 40% to 60%; or 45% to 65% of the methane ($CH_4$) in the gas stream provided to the reactor may be converted to products. In various instances, exemplary gas streams may comprise methane ($CH_4$) at no less than 1%; no less than 5%; no less than 10%; no less than 15%; no less than 16%; no less than 17%; no less than 18%; no less than 20%; no less than 25%; no less than 30%; no less than 40%; no less than 50%; no less than 60%; no less than 70%; no less than 75%; no less than 80%; no less than 90%; or no less than 95% of the methane ($CH_4$) in the gas stream provided to the reactor may be converted to products.

In some instances, exemplary method 300 may further comprise recycling unreacted gases back to the first inlet of the reactor (operation 310).

V. EXPERIMENTAL EXAMPLES

Without limiting the scope of the instant disclosure, experimental examples of embodiments discussed above were prepared and the results are discussed below.

The following examples demonstrate the conversion of methane in a dielectric barrier discharge reaction for the production of aromatics over different catalytic materials and the influence of bulk gas temperature of the reaction over conversion and product distributions.

Example 1

An A/C power source was used to supply a plasma power input of 10 W at a fixed frequency of 20 kHz. The applied voltage to obtain this plasma power across the inner and outer electrode ranged between 6-9 kV. The discharge gap of the reactor was fixed at 1.5 mm. A feed flowrate of 50 $mL \cdot min^{-1}$ was supplied to the reactor controlled by the use of mass flow controllers, and the composition of this feed was comprised of 50% $CH_4$ and 50% $N_2$. The effluent gas resulting from the reaction in the discharge zone was further analyzed utilizing an on-line gas chromatographer (GC) equipped with a thermal conductivity detector (TCD), flame ionization detector (FID), and a photoionization detector (PID). The effluent stream resulting of the reaction in the discharge zone was heated to a temperature range of 120-130° C., to prevent condensation of the products. In order to quantify the initial and final compositions for both reactants and products, external calibration curves were built. To calculate the conversion of $CH_4$, equation (1) was utilized, while equation (2) was used to measure carbon selectivities, and equation (3) to calculate production rates. This example illustrates methane conversion in a dielectric barrier discharge reactor in the absence of a catalytic material, at a constant reaction temperature of 300° C. Using equation (1), $CH_4$ conversion after 5 minutes of time on stream obtained under these conditions was 14.49±0.32%.

$$X_{CH_4}(\%) = \frac{\text{moles of } CH_4 \text{ reacted } (\text{moles min}^{-1})}{CH_4 \text{ fed } (\text{moles min}^{-1})} \times 100 \quad (1)$$

$$r(\text{moles min}^{-1} g^{-1}) = \frac{\text{molar flow rate of product (moles min}^{-1})}{\text{amount of catalyst (g)}} \quad (2)$$

$$\text{carbon selectivity (\%)} = \frac{FID \text{ area for } C_xH_y(a.u)}{\text{Sum of } FID \text{ areas for hydrocarbon products } (a.u)} \times 100 \quad (3)$$

Table 1 depicts the product distribution obtained as a result of methane conversion in the dielectric barrier discharge reactor. In the absence of a catalyst, no aromatic products were obtained under these conditions, as seen in Table 1. In addition, ethane ($C_2H_6$) was the predominant product of the reaction, with a selectivity of 50.63%. Other hydrocarbon products were present as a result of the conversion of methane, such as propane ($C_3H_8$), ethylene ($C_2H_4$), acetylene ($C_2H_2$) and species containing at least 4 carbon atoms ($C_4$). As shown in Table 1, 0.51% of the products formed were unknown (peaks present in the GC trace, but not identified). The carbon balance obtained for this reaction was 91.91%. In addition, carbon formation results from the conversion of methane in the dielectric barrier discharge reactor, which is reflected by the calculated carbon balance.

TABLE 1

Carbon selectivities obtained for 50 mol % $CH_4$ and 50 mol % $N_2$ reaction mixture at a fed flowrate of 50 mL · $min^{-1}$, plasma power input of 10 W at a constant frequency of 20 kHz, at 300° C. and 1 atm.

| Products | Selectivity (%) |
|---|---|
| $C_2H_4$ | 7.24 |
| $C_2H_6$ | 50.63 |
| $C_2H_2$ | 5.52 |
| $C_3H_8$ | 28.24 |
| benzene | 0.00 |
| toluene | 0.00 |
| CO/$CO_2$ | 0.00 |
| $C_4$ | 7.88 |
| unknowns | 0.51 |

Example 2

The experimental conditions were maintained the same as in Example 1, however, this example describes the use of Mobil-type five (MFI) zeolites for the conversion of methane in a dielectric barrier discharge reactor. Specifically, the proton form of ZSM-5 (H-ZSM-5) was used for the reaction. To obtain this material, the $NH_4$-ZSM-5 (Si/Al=11.5, Zeolyst International) form was subjected to calcination at 600° C. to generate the H-ZSM-5 catalyst. Measured conversion for methane after 5 minutes of time on stream was 16.20±1.13%. In the presence of H-ZSM-5, aromatic species were detected utilizing the on-line GC. As shown in Table 2, the obtained carbon selectivity for benzene was 0.92% and 2.42% for toluene, while the measured carbon balance for this reaction was 91.39%.

TABLE 2

Carbon product selectivities obtained for 50 mol % $CH_4$ and 50 mol % $N_2$ reaction mixture over H-ZSM-5 (Si/Al = 11.5) at a fed flowrate of 50 mL · $min^{-1}$, plasma power input of 10 W at a constant frequency of 20 kHz, at 300° C. and 1 atm.

| Products | Selectivity (%) |
|---|---|
| $C_2H_4$ | 9.30 |
| $C_2H_6$ | 48.80 |
| $C_2H_2$ | 3.46 |
| $C_3H_8$ | 26.88 |
| benzene | 0.92 |
| toluene | 2.42 |
| CO/$CO_2$ | 2.37 |
| $C_4$ | 5.85 |
| unknowns | 0.00 |

Under the conditions studied, ethane ($C_2H_6$) was the predominant product of the reaction, with a selectivity of 48.80%. In addition, no unknown species were detected as a product of the reaction.

Example 3

The experimental conditions stated in Example 1 were maintained, however, this example describes the use of molybdenum (Mo) loaded onto the proton active form of ZSM-5. The metal was loaded on H-ZSM-5 utilizing the incipient wetness impregnation technique, where the composition of Mo on ZSM-5 was fixed at 2 wt. %. Following incipient wetness impregnation, the catalyst was subjected to calcination under static air at 550° C. The performance of the catalyst for methane conversion was tested in a dielectric barrier discharge reactor at 300° C. Measured methane conversion after 5 minutes of time on stream was 14.50±2.47%. Aromatic products were detected for the conversion of methane over 2 wt. % Mo/H-ZSM-5 catalyst in a dielectric barrier discharge reactor (Table 3). Here, benzene selectivity was found to be 0.50%, while toluene selectivity had a value of 1.06%. Methane conversion over Mo/H-ZSM-5 leads predominantly to formation of $C_2$ hydrocarbons under the studied conditions. The carbon balance for this reaction was measured to be 92.64%.

TABLE 3

Carbon selectivities obtained for 50 mol % $CH_4$ and 50 mol % $N_2$ reaction mixture over 2 wt. % Mo/H-ZSM-5 (Si/Al = 11.5) at a fed flowrate of 50 mL · $min^{-1}$, plasma power input of 10 W at a constant frequency of 20 kHz, at 300° C. and 1 atm.

| Products | Selectivity (%) |
|---|---|
| $C_2H_4$ | 10.85 |
| $C_2H_6$ | 53.21 |
| $C_2H_2$ | 0.82 |
| $C_3H_8$ | 26.68 |
| benzene | 0.50 |
| toluene | 1.06 |
| CO/$CO_2$ | 1.62 |
| $C_4$ | 5.27 |
| unknowns | 0.00 |

Example 4

The experimental conditions stated in Example 1 were maintained, however, the reaction temperature was further adjusted to 400° C. The catalytic materials used in Example 2 and 3 (i.e., H-ZSM-5 and Mo/H-ZSM-5) were tested for the conversion of methane in a dielectric barrier discharge reactor under the same conditions. The measured conversion for methane obtained after 5 minutes of time on stream over H-ZSM-5 and Mo/H-ZSM-5 were 13.97±0.29% and 11.99±1.01%. With the use of equation (2), the total aromatic production (i.e., benzene and toluene) over both H-ZSM-5 and Mo/H-ZSM-5 were calculated under the studied conditions.

Table 4 shows the calculated total aromatic production rates, where a value of 0.0488 mmol $g^{-1}$ $min^{-1}$ was obtained over H-ZSM-5, while 0.0275 mmol $g^{-1}$ $min^{-1}$ was measured over 2 wt. % Mo/H-ZSM-5.

TABLE 4

Total aromatic production rates obtained for 50 mol % $CH_4$ and 50 mol % $N_2$ reaction mixture over H-ZSM-5 (Si/Al = 11.5) and 2 wt. % Mo/H-ZSM-5 (Si/Al = 11.5) at a fed flowrate of 50 mL · $min^{-1}$, plasma power input of 10 W at a constant frequency of 20 kHz, at 400° C. and 1 atm.

| Catalyst | Aromatic Production (mmol $g^{-1}$ $min^{-1}$) |
|---|---|
| H-ZSM-5 | 0.0488 |
| 2 wt. % Mo/H-ZSM-5 | 0.0275 |

Table 5 shows the carbon selectivities obtained over both catalytic materials. The benzene and toluene selectivity over H-ZSM-5 were 1.64% and 2.53%, respectively. For 2 wt. % Mo/H-ZSM-5, the benzene and toluene selectivity obtained were 1.72% and 1.98%.

TABLE 5

Carbon selectivities obtained for 50 mol % $CH_4$ and 50 mol % $N_2$ reaction mixture over H-ZSM-5 (Si/Al = 11.5) and 2 wt. % Mo/H-ZSM-5 (Si/Al = 11.5) at a fed flowrate of 50 mL · $min^{-1}$ plasma power input of 10 W at a constant frequency of 20 kHz, at 400° C. and 1 atm.

| | Selectivity (%) | |
|---|---|---|
| Products | H-ZSM-5 | 2 wt. % Mo/H-ZSM-5 |
| $C_2H_4$ | 13.19 | 13.84 |
| $C_2H_6$ | 50.86 | 57.00 |
| $C_2H_2$ | 2.64 | 0.62 |
| $C_3H_8$ | 23.89 | 20.68 |
| benzene | 1.64 | 1.72 |
| toluene | 2.53 | 1.98 |
| $CO/CO_2$ | 1.03 | 1.68 |
| $C_4$ | 3.92 | 2.47 |
| unknowns | 0.29 | 0.00 |

Example 5

The experimental conditions were maintained as stated in Example 1, however, the reaction temperature was increased to 500° C. The catalytic materials used in Example 2, 3 and 4 (i.e., H-ZSM-5 and Mo/H-ZSM-5) were tested for the conversion of methane in a dielectric barrier discharge reactor under the same conditions. The measured conversion for methane obtained after 5 minutes of time on stream over H-ZSM-5 and Mo/H-ZSM-5 were 17.43±3.52% and 15.81±1.14%. The total aromatic production was calculated using equation (2) over both H-ZSM-5 and Mo/H-ZSM-5 and shown in Table 6, where 0.0747 mmol $min^{-1}$ were obtained over H-ZSM-5, and 0.1214 mmol $g^{-1}$ $min^{-1}$ were obtained over 2 wt. % Mo/H-ZSM-5.

TABLE 6

Total aromatic production rates obtained for 50 mol % $CH_4$ and 50 mol % $N_2$ reaction mixture over H-ZSM-5 (Si/Al = 11.5) and 2 wt. % Mo/H-ZSM-5 (Si/Al = 11.5) at a fed flowrate of 50 mL · $min^{-1}$, plasma power input of 10 W at a constant frequency of 20 kHz, at 500° C. and 1 atm.

| Catalyst | Aromatic Production (mmol $g^{-1}$ $min^{-1}$) |
|---|---|
| H-ZSM-5 | 0.0747 |
| 2 wt. % Mo/H-ZSM-5 | 0.1214 |

Table 7 depicts the carbon selectivities obtained over both catalytic materials. The benzene and toluene selectivity obtained over H-ZSM-5 were 3.98% and 2.26%, respectively. The benzene and toluene selectivity obtained over the 2 wt. % Mo/H-ZSM-5 were 10.24% and 2.99%.

TABLE 7

Carbon selectivities obtained for 50 mol % $CH_4$ and 50 mol % $N_2$ reaction mixture over H-ZSM-5 (Si/Al = 11.5) and 2 wt. % Mo/H-ZSM-5 (Si/Al = 11.5) at a fed flowrate of 50 mL · $min^{-1}$, plasma power input of 10 W at a constant frequency of 20 kHz, at 500° C. and 1 atm.

| | Selectivity (%) | |
|---|---|---|
| Products | H-ZSM-5 | 2 wt. % Mo/H-ZSM-5 |
| $C_2H_4$ | 22.00 | 15.79 |
| $C_2H_6$ | 48.41 | 51.91 |
| $C_2H_2$ | 0.67 | 0.00 |
| $C_3H_8$ | 21.62 | 16.73 |
| benzene | 3.98 | 10.24 |
| toluene | 2.26 | 2.99 |
| $CO/CO_2$ | 0 | 1.13 |
| $C_4$ | 0.81 | 1.2 |
| unknowns | 0.25 | 0.00 |

The invention claimed is:

1. A method for processing a gas stream, the method comprising:

providing the gas stream to a reactor, the gas stream comprising methane and being provided at a first flowrate;

contacting the gas stream with a catalyst material in a reaction zone of the reactor, the catalyst material comprising molybdenum (Mo) at 2% by weight (wt %) to 5 wt %;

providing a voltage to an inner electrode disposed within the reaction zone, thereby generating a plasma in the reaction zone across a discharge gap;

maintaining a temperature in the reaction zone of no less than 300° C. and no greater than 700° C.; and collecting products from an outlet of the reactor.

2. The method according to claim 1, further comprising providing nitrogen ($N_2$) at a second flowrate to a second inlet of the reactor, thereby forming a gas composition, wherein the first flowrate is 5 standard cubic centimeters per minute ($cm^3$/min) to 11,304 $cm^3$/min and the second flowrate is 4 $cm^3$/min to 10,174 $cm^3$/min.

3. The method according to claim 2, the gas composition comprising, by mol %:

1% to 99% methane ($CH_4$); and

99% to 1% nitrogen ($N_2$).

4. The method according to claim 1, the catalyst material including a zeolite-based material comprising silicon (Si) and aluminum (Al), the zeolite-based material having: a silicon (Si) to aluminum (Al) atomic ratio of 11.5 to 300; and a pore size of 4 Å to 20 Å.

5. The method according to claim 4, the zeolite-based material comprising $Na_nAl_nSi_{96}$-$nO_{192}$·$16H_2O$, where n is greater than 0 and less than 27.

6. The method according to claim 5, wherein the temperature in the reaction zone is no greater than 500° C.

7. The method according to claim 1, wherein the gas stream further comprises at least one of ethane, propane, or butane.

8. The method according to claim 1, wherein the voltage provided is no less than 6 kV and no greater than 9 kV, and the plasma power input is 9 W to 11 W.

9. The method according to claim 1, wherein the voltage is provided at a frequency of 2 kHz to 700 kHz, and wherein the voltage is provided from an A/C power source.

10. The method according to claim 1, further comprising:

attenuating an output signal from the A/C power source;

providing the attenuated output signal to an oscilloscope; and with the oscilloscope, determining a plasma power.

11. The method according to claim 1, the products comprising benzene, toluene, and xylenes.

12. A system for processing a gas stream comprising methane, comprising:

a reactor comprising:

a first inlet in fluid communication with a gas stream source, the gas stream source comprising methane;

a reaction zone in fluid communication with the first inlet, the reaction zone comprising:

catalyst material arranged as a catalyst bed, the catalyst material comprising molybdenum (Mo) at 2% by weight (wt %) to 5 wt %;

an inner electrode;

an outer electrode; and an inner volume defined between the inner electrode and the outer electrode;

a reactor temperature regulation unit arranged to maintain a predetermined reaction zone temperature of no less than 300° C. and no greater than 700° C.; and an outlet in fluid communication with the reaction zone;

an analysis unit configured to receive fluid from the reactor outlet; and a voltage supply and monitor system in electrical communication with the inner electrode and with the outer electrode.

13. The system according to claim 12, the reactor further comprising a second inlet in fluid communication with a nitrogen ($N_2$) gas source, the first inlet and the second inlet being positioned at an upper portion of the reactor; and the outlet being positioned at a lower portion of the reactor.

14. The system according to claim 12, the reaction zone being cylindrical, the outer electrode annularly defining an exterior of the reaction zone, the reaction zone having a discharge gap of 0.1 mm to 150 mm.

15. The system according to claim 12, the inner electrode comprising tungsten and the outer electrode comprising stainless steel.

16. The system according to claim 12, the catalyst bed occupying between one half and two-thirds of a volume of the reaction zone.

17. The system according to claim 12, the reactor temperature regulation unit arranged to maintain a predetermined reaction zone temperature of no greater than 500° C.

18. The system according to claim 12, the system further comprising a gas chromatograph (GC) in fluid communication with the reactor outlet, the gas chromatograph (GC) comprising a thermal conductivity detector (TCD), a flame ionization detector (FID), and a photoionization detector (PID).

19. The system according to claim 12, the voltage supply and monitor system comprising:

an alternating current (AC) power source in electrical communication with the inner electrode;

an oscilloscope;

a voltage attenuator in electrical communication with the A/C power source and the oscilloscope; and a monitor capacitor in electrical communication with the outer electrode and the oscilloscope.

* * * * *